United States Patent [19]
Gibson et al.

[11] 3,957,583
[45] May 18, 1976

[54] APPARATUS AND PROCESS FOR DETERMINING THE SUSCEPTIBILITY OF MICROORGANISMS TO ANTIBIOTICS

[75] Inventors: Sandra F. Gibson, St. Louis County; Norman L. Fadler, St. Peters, both of Mo.

[73] Assignee: McDonnell Douglas Corporation, St. Louis, Mo.

[22] Filed: Dec. 2, 1974

[21] Appl. No.: 528,840

[52] U.S. Cl. .................... 195/103.5 R; 23/253 R; 23/259; 195/127; 195/139
[51] Int. Cl.² .......................................... C12K 1/04
[58] Field of Search .................. 23/253 R, 259 R; 195/103.5 R, 127, 139

[56] References Cited
UNITED STATES PATENTS

| | | | |
|---|---|---|---|
| 3,370,175 | 2/1968 | Jordon et al. ................. | 195/103.5 R |
| 3,509,026 | 4/1970 | Sanders ........................ | 195/103.5 R |

Primary Examiner—A. Louis Monacell
Assistant Examiner—Robert J. Warden
Attorney, Agent, or Firm—Gravely, Lieder & Woodruff

[57] ABSTRACT

A process for determining the susceptibility of microorganisms to antibiotics involves introducing a diluted specimen into discrete quantities of a selective culture medium which favors a specific microorganism in that the microorganism is sustained by the medium and when so sustained will change the optical characteristics of the medium. Only the specific microorganism will alter the optical characteristics. Some of the discrete quantities are blended with known antibiotics, while at least one is not. If the specimen contains the microorganisms favored by the selective medium, the optical characteristics of the discrete quantity of pure selective medium, that is the one without antibiotics, will change. If the antibiotics in any of the other discrete quantities are ineffective against the favored microorganisms, the optical characteristics of those quantities will likewise change. No change in the optical characteristics of a discrete quantity indicates that the favored microorganism is susceptible to the antibiotic in the quantity.

15 Claims, 4 Drawing Figures

U.S. Patent    May 18, 1976    3,957,583
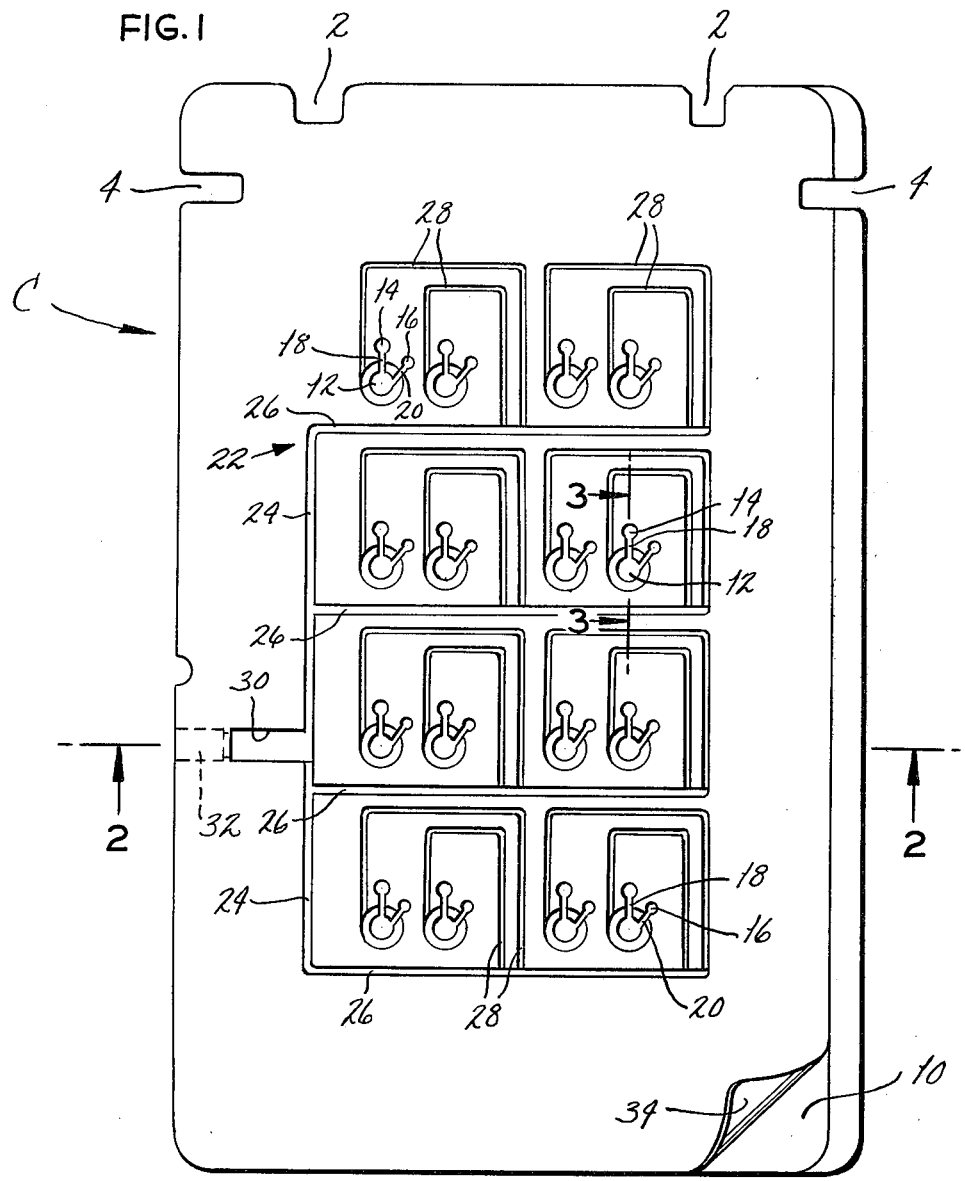
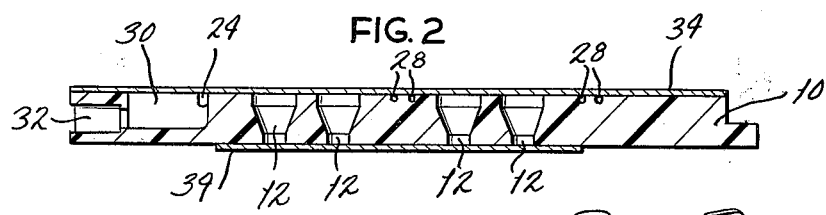
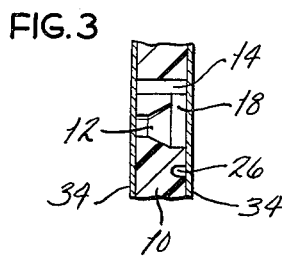
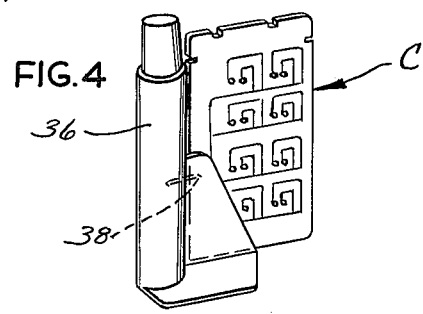

3,957,583

APPARATUS AND PROCESS FOR DETERMINING THE SUSCEPTIBILITY OF MICROORGANISMS TO ANTIBIOTICS

The invention described herein was made in the performance of work under NASA Contract No. NAS 9-11877 and is subject to the provisions of Section 305 of the National Aeronautics and Space Act of 1958 (72 Stat. 435; 42 U.S.C. 2457).

BACKGROUND OF THE INVENTION

This invention relates in general to determining the effectiveness of antibiotics on microorganisms, and more particularly to an apparatus and process for conducting antibiotic susceptibility tests without isolating microorganisms.

The routine clinical procedure for determining the sensitiveness of microorganisms to antibiotics is basically a two-step operation which requires a minimum of 48 hours to complete. The first step involves growing the organism from a sample, and in that case the microorganism is isolated. The second step involves subjecting the isolated microorganism to various antibiotics to determine which one inhibits growth of the microorganism. Of course, during the time required to conduct the susceptibility tests, a patient's condition may worsen or change drastically. It is, therefore, imperative to determine the proper antibiotic and to administer it as soon as possible.

SUMMARY OF THE INVENTION

One of the principal objects of the present invention is to provide an apparatus and process for conducting antibiotic susceptibility tests in a relatively short time, which may be as little as eight hours. Another object is to provide an apparatus and process of the type stated in which the clinical sample as examined directly without isolating the suspected microorganism. Another object is to provide an apparatus which is simple to operate and does not require highly skilled technicians. These and other objects and advantages will become apparent hereinafter.

The present invention is embodied in an apparatus and process which basically involves introducing a specimen into blends of a selective culture medium and known antibiotics. If the specimen contains a microorganism which is favored by the culture medium of a blend, and the microorganism is not susceptible to the antibiotic, the optical characteristics of the blend will change. The invention also consists in the parts and in the arrangements and combinations of parts hereinafter described and claimed.

DESCRIPTION OF THE DRAWINGS

In the accompanying drawings which form part of the specification and wherein like numerals and letters refer to like parts wherever they occur:

FIG. 1 is a plan view of a cassette constructed in accordance with and embodying the present invention;

FIG. 2 is a sectional view taken along line 2—2 of FIG. 1;

FIG. 3 is a sectional view taken along line 3—3 of FIG. 1, and

FIG. 4 is a perspective view showing the diluted specimen being introduced into the cassette.

DETAILED DESCRIPTION

Referring now to the drawings (FIG. 1), C designates a cassette for conducting antibiotic susceptibility tests, that is tests to determine the effect of known antibiotics contained within the cassette C have on a microorganism introduced into the cassette C. The cassette C also enables one to identify the microorganism. The cassette C is rectangular in shape, preferably measuring 2.24 inches by 3.59 inches, and being 0.125 inches thick. Along one of its shorter margins it has two spaced apart locating indentations 2, while each of its longer margins has a gripping indentation 4 opening outwardly therefrom near the margin from which the locating indentations 2 open. The locating and gripping indentations 2 and 4 enable the cassette C to be handled mechanically for viewing and other purposes. Adjacent to one of its longer margins, the cassette C has a suitable identification code on one of the major surfaces thereof, and this code identifies the patient, the type of culture medium, the date of the sample and the like.

The cassette C includes a rigid body in the form of a plastic plate 10 which is the same size and shape as the cassette C and hence includes the indentations 2 and 4. The plate 10 has growth wells 12 which are arranged in a plurality of transversely extending groups or rows. Adjacent to each growth well 12 the plate 10 is further provided with a pair of overflow cavities 14 and 16, and these cavities are connected with the wells 12 through overflow channels 18 and 20. The wells 12 and overflow cavities 14 and 16 extend completely through the plate 10 and hence open out of both major surfaces of it. The channels 18 and 20 likewise extend completely through the plate 10. Each well 12 is designated by a number marked on the face of the plate 10.

The wells 12 are all connected to a filling passage 22 which is merely a groove opening out of only one face of the plate 10. The filling passage 22 includes a longitudinal feeder branch 24 which extends along one of the longer side edges of the plate 10, being parallel to that side edge. Intersecting the longitudinal feeder branch 24 are a plurality of transverse lateral branches 26, there being a lateral branch 26 for each row of wells 12. The individual wells 12 are connected with the lateral branches 26 through terminal branches 28 which are long enough to prevent the contents of adjacent wells 12 from mixing. The terminal branches 28 lead into the wells 12 themselves and not the overflow cavities 14 and 15 for those wells.

Between the longitudinal branch 24 of the filling passage 22 and the adjacent side edge which parallels that branch 24, the plate 10 is provided with a filling port 30 which opens both into the longitudinal passage 24 and out of the side edge. The outer portion of the filling port 30 is occupied by a tightly fitted septum 32.

All of the growth wells 12 in the cassette C contain the same selective culture medium which favors a specific microorganism in the sense that only that microorganism will be sustained by the culture medium and when so sustained will change the light transmitting characteristics of the culture medium. The culture medium is freeze-dried and is rehydrated contemporaneously with the introduction of the specimen in it. Actually, the culture medium undergoes an optical change as a result of the metabolic action of the specific microorganism, and while the favored microorganism will grow or multiply in the selective medium, growth is not necessary to effect the optical change. Only the specific microorganism will live and propogate in the culture medium and will further cause the optical change. Hence, when the optical change is observed, it is apparent that the specific microorganism is living in the culture medium. Since the culture medium is freeze-dried, the cassette C may be stored for relatively long periods of time. However, the culture medium must be rehydrated before it is capable of promoting the growth of the specific microorganism and changing its light transmitting characteristics in response to that growth. The selective culture medium is the same for all wells 12 in the cassette C, but may vary from cassette to cassette.

Suitable selective culture media are disclosed in the co-pending application of Clifton Aldridge, Jr., et al, Ser. No. 461,249, filed Apr. 4, 1974 and entitled PROCESS AND APPARATUS FOR ANALYZING SPECIMENS FOR THE PRESENCE OF MICROORGANISMS THEREIN.

In at least one of the wells 12 the selective culture medium exists by itself. The culture medium in each of the remaining wells 12 has an antibiotic blended with it. The antibiotics may vary from well 12 to well 12, and the two different wells 12 may have the same antibiotic but at different strengths. Thus, the microorganisms will not live or propogate in those wells 12 containing an antibiotic to which the favored microorganism is susceptible, provided the antibiotic is present in the sufficient strength.

Each major surface of the plate 10 is covered with a transparent tape 34 which is wide enough and long enough to completely cover and close all of the wells 12, the overflow cavities 14 and 16, the overflow channels 18 and 20 and the filler passageway 22. The tape 34 has the capability of admitting air to the wells 12, but preventing water and microorganisms from escaping FEP 5430 tape manufactured by the 3M Company is suitable for this purpose.

OPERATION

To conduct an antibiotic susceptibility test with the cassette C, a specimen suspected of containing a harmful microorganism is diluted in a predetermined quantity of water contained in a reservoir 36. The lower end of the reservoir 36 has a needle 38 projected from it, and this needle is inserted through the septum 32 so that the filler passage 22 and the interior of the reservoir 36 are in communication (FIG. 4).

Once the reservoir and cassette C are connected through the needle 38 a vacuum on the order of 40 mm Hg is drawn in the filler passage 22 and wells 12, of the cassette C by connecting a vacuum pump to the upper end of the reservoir 36. Thus, the interior of the cassette C is evacuated through the water in the reservoir 36.

Upon obtaining the desired vacuum, the upper end of the reservoir 36 is immediately vented to the atmosphere so that the pressure on the diluent mixture forces that mixture into the cassette C. Thus, the diluent mixture takes the place of the evacuated air. Indeed, the diluent mixture flows quite rapidly through the filler passage 22, and thence into the wells 12 where it rehydrates the culture medium therein. The diluent mixture and culture medium furthermore flows over into the overflow channels 18 and 20 and the overflow cavities 14 and 16 at their ends. Any air remaining in the passageway 22 and wells 12 will collect in the overflow cavities 14 and 16. It should be noted that while the tape 34 is capable of admitting air to the wells 12, its pores are so small that the vacuum created by the pump exists long enough to achieve a proper fill upon release of the vacuum.

The cassette C is then placed in a heated environment to incubate any microorganisms in the wells 12.

Should the culture medium for the cassette C favor the microorganism in the diluent mixture, the microorganism will remain viable and will live in the well 12 containing the pure culture medium. Hence, the microorganism will grow and its metabolic action will cause the culture medium to undergo a change in optical characteristics. Since the microorganism favored by the culture medium is known, as is the nature of the change in optical characteristics effected by the microorganism, the change in the optical characteristics of the well 12 containing the pure culture medium serves to identify the organism.

Not only does the well 12 containing the pure culture medium undergo a change in optical characteristics, but so does every other well 12 which contains an antibiotic to which the microorganism is not susceptible. Also, any well 12 containing an antibiotic in inadequate strength will also undergo a change in optical characteristics. In other words, the favored microorganism will live and grow in every well 12 where the antibiotic is not effective or not at sufficient strength levels. However, the absence of any change in the optical characteristics indicates that the antibiotic is effective against the microorganism. Since the antibiotic in each well 12 is known, it is possible to determine which antibiotics will combat the microorganism.

Meaningful changes in optical characteristics of the wells 12 occur at a minimum of 2 hours from the time the diluent mixture is introduced and incubated and at a maximum of 14 hours. The changes may be observed with the naked eye or with an electro-optical detector of the type disclosed in U.S. patent application Ser. No. 461,249, previously referred to herein. The electro-optical detector projects light through the wells 12 and measures the intensity of the light beyond the wells 12. A significant decrease in intensity indicates growth or metabolic action of the favored microorganism in a well 12 and hence the antibiotic in that well 12 is not effective against the favored microorganism.

EXAMPLE I

Coliform broth or medium disclosed in U.S. application Ser. NO. 461,249 is used to detect coliform organisms (Escherichia coli) which are found primarily in fecal specimens and cause enteric infection. The broth is prepared by dissolving 10 g. of lactose and 10 g. of gelysate in 1.0 liter of distilled water. Next, HCl or NaOH are added to bring the pH to 7.4. Thereafter, 10 g. of sodium desoxycholate are added. The mixture may be heated to dissolve the ingredients, but should not be brought to a boil. Finally, the solution is sterilized by filtering and 13.3 mg. of brilliant green are added. The foregoing broth is freeze-dried to form the selective medium which is loaded in one of the wells 12 in its pure form.

For each liter of medium prior to freeze-drying one of the following antibiotics may be added in these concentrations to form a blend for other wells 12:

| Ampicillin | 0.03 | g. |
| Cephalothin | 0.1 | g. |

-continued

| | | |
|---|---|---|
| Colistin | 0.01 | g. |
| Tetracycline | 0.015 | g. |
| Nitrofurantoin | 0.015 | g. |
| Kanamycin | 0.01 | g. |
| Streptomycin | 0.03 | g. |
| Gentamicin | 0.01 | g. |

For other selective media, similar concentrations are used.

What is claimed is:

1. A device for conducting antibiotic susceptibility tests on clinical specimens, said device comprising: a plate having detection wells therein and a filler passage leading to the wells, the plate also having an overflow of cavities communicating with each detection well downstream from the entry of the filler passage into such wells; means for isolating the wells, filler passage, and overflow cavities from the surrounding atmosphere; and a blend of culture medium and known antibiotics in at least some of the detection wells, the culture medium being sensitive to the microorganisms in the sense that the optical characteristics of the culture medium change when a microorganism is sustained in the culture medium, the culture medium further being selective in that it undergoes a change in optical characteristics only when a specific microorganism is sustained by it.

2. A device for conducting antibiotic susceptibility tests on clinical specimens, said device comprising: a rigid body having wells therein, the body also having a filling port opening out of an exterior surface thereof so that the specimen diluted in water can be introduced into the body and a filler passage leading from the port to the wells for directing the diluted specimen to the wells, the rigid body further having overflow cavities communicating with each well downstream from the entry of the filler passage into such wells; means for isolating the interiors of the wells, the overflow cavities, and the filler passage from the surrounding atmosphere to prevent the entry of contaminants into them; a selective culture medium in at least one of the wells, the selective culture medium favoring a specific microorganism such that the optical characteristics of the culture medium changes when the favored microorganism is sustained within and nourished by the medium; and a blend of the selective culture medium and known antibiotics in at least some of the remaining wells, whereby the effectiveness of the known antibiotics on the specific microorganism can be determined by observing the wells in which said antibiotics exist.

3. A process for determining the susceptibility of a specific microorganism to antibiotics, said process comprising: evacuating air from a well in which a selective culture medium is contained and from wells in which blends of the selective culture medium and known antibiotics are contained, said culture medium favoring the specific microorganism such that the light-transmitting characteristics of a mixture of the culture medium and water will change when the favored microorganism is sustained within and nourished by the medium; replacing the evacuated air with a diluent mixture composed essentially of a clinical specimen diluted in water whereby the diluent mixture mixes with the selective culture medium in the wells; incubating the mixture of the blend and diluent mixture; and observing the wells for a change in the light-transmitting characteristics thereof.

4. A process according to claim 3 wherein the culture medium is freeze-dried and the water of the diluent mixture rehydrates the medium.

5. A process according to claim 3 wherein wells are observed by projecting light through them and measuring the intensity of the light leaving the wells.

6. A process for examining a clinical specimen for the presence of a specific microorganism therein and for determining the susceptibility of the microorganism to various antibiotics, said process comprising: diluting the specimen in water, mixing the diluted specimen with discrete quantities of a culture medium which is selective as to the specific organism in that its light-transmitting characteristics will change when the specific microorganism is sustained within and nourished by the medium, some of the discrete quantities having antibiotics therein, at least one of the discrete quantities being free of antibiotics; incubating the mixtures of the discrete quantities of culture medium and the diluted specimens; and observing the incubated quantities of culture medium and diluent mixture for a change in the light-transmitting characteristics thereof.

7. A device for conducting antibiotic susceptibility tests on clinical specimens, said device comprising: a plate having a plurality of wells opening out of a surface thereon with the wells being visible on both sides of the device so that light will pass through the device at the wells, the plate also having a filling port and a filler passage leading from the filling port to the wells; means for closing the filling port; a selective culture medium in the wells, the culture medium being selective in the sense that the light-transmitting characteristics of the culture medium will change when the microorganism to which it is specific is introduced into a mixture of the medium and water; known antibiotics blended with the culture medium in at least some of the wells; and means at the surface of the plate out of which the wells open for closing the ends of the wells at the surface to isolate the wells, the culture medium in the wells, and the filler passage from the surrounding atmosphere, the closing means being capable of transmitting light through the wells, the closing means further having pores capable of admitting air to the wells, but small enough to prevent water and microorganisms from escaping from the wells.

8. A device according to claim 7 wherein the same selective culture is in all of the wells, but the antibiotics are different in at least some of the wells.

9. A device according to claim 8 wherein at least one of the wells contains only the selective culture medium, and not an antibiotic.

10. A device according to claim 9 wherein the culture medium in the wells is freeze-dried.

11. A device according to claim 7 wherein the means closing the ends of the walls is tape which is extended across the plate and adhered to the surface thereof, the tape being capable of admitting oxygen to the wells to sustain the microorganism in the culture medium.

12. A device according to claim 7 where the means for closing the filling port is a septum fitted tightly into the filling port.

13. A device according to claim 7 wherein the means for closing the ends of the wells is at both ends of the wells.

14. A device according to claim 13 wherein the means for closing the ends of the wells are strips of tape which extend over and are adhered to the surfaces of the plate out of which the wells open.

15. A device for conducting antibiotic susceptibility tests on clinical specimens, said device comprising: a generally rectangular plate having parallel major surfaces and a peripheral edge, the plate having a plurality of wells which are arranged in transverse rows and extend from one surface area to the other, the plate also having a filling port which opens out of the peripheral edge, a feeder groove connected with the filling port and extending longitudinally past the ends of some of the rows, lateral grooves extending transversely from the feeder groove with at least some of the lateral grooves passing between adjacent rows of wells, and terminal grooves connecting the lateral grooves with the wells, there being a separate terminal groove for each well and the feeder, lateral, and terminal grooves all opening out of one major surface of the plate; means for closing the filling port; a first tape extended over said one major surface area out of which the wells and grooves open and closing the ends of the wells and the sides of the grooves at that major surface and a second tape extended over the other major surface and closing the other ends of the wells, both of the tapes being transparent and adhered tightly to the surfaces over which they extend, whereby the wells and grooves are isolated from the surrounding atmosphere, at least one of the tapes having pores therein capable of admitting air to the wells but small enough to prevent water and microorganisms from escaping from the wells; a selective culture medium in at least one of the wells, the culture medium being selective in the sense that the light transmitting characteristics of the culture medium will change when the microorganism to which it is specific is introduced into a mixture of the culture medium and water; and blends of the same selective culture medium and various known antibiotics in the other wells.

* * * * *

UNITED STATES PATENT OFFICE
CERTIFICATE OF CORRECTION

Patent No. 3,957,583    Dated    May 18, 1976

Inventor(s)  Sandra F. Gibson and Norman L. Fadler

It is certified that error appears in the above-identified patent and that said Letters Patent are hereby corrected as shown below:

Column 1, line 39, delete "as" and insert - - - is - - - in its place.

Column 5, line 14, (line 4 of claim 1) delete "an."

Column 5, line 15, (line 5 of claim 1) delete "of."

Signed and Sealed this
Tenth Day of August 1976

[SEAL]

Attest:

RUTH C. MASON
Attesting Officer

C. MARSHALL DANN
Commissioner of Patents and Trademarks